United States Patent [19]

Leipold

[11] Patent Number: 4,584,189

[45] Date of Patent: * Apr. 22, 1986

[54] BACTERICIDAL TOOTHPASTES

[75] Inventor: Dianne P. Leipold, Newark, Del.

[73] Assignee: Hercules Incorporated, Wilmington, Del.

[*] Notice: The portion of the term of this patent subsequent to Nov. 27, 2001 has been disclaimed.

[21] Appl. No.: 655,836

[22] Filed: Sep. 28, 1984

[51] Int. Cl.$^4$ .......................... A61K 7/16; A61K 7/22
[52] U.S. Cl. .......................................... 424/54; 424/49
[58] Field of Search .................................... 424/49, 54

[56] References Cited

U.S. PATENT DOCUMENTS

| | | | |
|---|---|---|---|
| 3,934,000 | 1/1976 | Barth | 424/49 |
| 4,228,277 | 10/1980 | Landoll | 536/90 |
| 4,370,314 | 1/1983 | Gaffar | 424/54 |
| 4,485,089 | 11/1984 | Leipold | 424/49 |

*Primary Examiner*—Shep K. Rose
*Attorney, Agent, or Firm*—Joanne L. Horn

[57] ABSTRACT

Disclosed are dentifrice compositions comprising a cationic bactericide, water, a dental abrasive, and a hydrophobically modified hydroxyethyl cellulose thickener.

9 Claims, No Drawings

BACTERICIDAL TOOTHPASTES

The present invention relates to a dentifrice composition comprising a cationic bactericide, water, a dental abrasive, and a hydrophobically modified hydroxyethyl cellulose thickener. Such dentifrice compositions are commonly referred to as toothpastes.

Toothpastes are available in cream and gel form and typically contain abrasives. The opaque cream toothpastes contain insoluble inorganic salts, such as dicalcium phosphate dihydrate, calcium pyrophosphate, dicalcium pyrophosphate, tetrasodium pyrophosphate, calcium phosphate and calcium carbonate as the abrasive. Silica xerogels having an average particle size of approximately 2 to about 20 microns, preferably about 8 to 9 microns, a surface area of at least 200 $m^2/g$, and a bulk density of at least 0.15 $g/cm^3$ are used as abrasives in gel toothpastes.

The silica xerogels are able to provide the necessary abrasiveness since they do not hydrate in the presence of water.

The typical abrasive agents used in the cream toothpastes are not as abrasive as the silica xerogels used in the gel toothpaste. Hence, a lower concentration of the more abrasive silica xerogels can be used in the gel toothpastes, thereby allowing for the formation of a high humectant, low water, transparent gel toothpastes.

The abrasives are not necessary to remove plaque since this is accomplished by simple brushing. Instead, they are used to remove stains from the teeth and to polish the teeth. Unfortunately, however, the abrasives do not prevent plaque formation.

Since a reduction in plaque formation generally results in a reduction in dental cavities and in better dental health, there has been considerable interest recently in the development of toothpastes containing bactericides which will reduce the number of bacteria in the mouth. This, in turn, will reduce the amount of plaque formed.

Typical bactericides for toothpastes are cationic quaternary ammonium salt compounds having bactericidal activity such as those disclosed in U.S. Pat. No. 4,370,314, the disclosures of which are incorporated by reference. Generally, the cationic quaternary compounds are present in an amount from about 0.5% to about 1%, by weight of the total dentifrice composition.

The traditional abrasive-containing toothpastes also contain a thickener. The thickener of choice in cream or opaque toothpastes is sodium carboxymethyl cellulose (CMC). However, carrageenan is also used. Silica aerogels, precipitated silicas and pyrogenic silicas having an average particle size of approximately 4 microns, and dehydrated silica hydrogels having a bulk density of less than 0.13 $g/cm^3$ are the typical thickening agents for gel toothpastes. Silica aerogels hydrate and swell in the presence of water which accounts for their ability to thicken. CMC is commonly used in gel toothpastes, but not as a thickening agent, rather as a rheological modifier and as a water binder.

CMC is anionic polymer which is incompatible with the cationic bactericides. This incompatibility manifests itself in a long term, uncontrolled viscosity increase and in syneresis. Xanthan gum, an anionic polysaccharide containing a carboxylate group in the polymer repeat unit, is likewise incompatible with the cationic bactericidal compounds. However, xanthan is not used very often since it is more expensive than other available thickening agents.

The nonionic polymers generally used to thicken toothpastes, namely methyl cellulose, hydroxyethyl cellulose and hydroxypropyl cellulose, also have their drawbacks. Methyl cellulose gels at elevated temperatures. Hydroxyethyl cellulose does not prevent phase separation and syneresis. Hydroxypropyl cellulose is insoluble in toothpaste systems above about 45° C.

This invention provides a dentifrice composition or toothpaste comprising a cationic bactericide, water, a dental abrasive and a hydrophobically modified hydroxyethyl cellulose thickener. The compositions of this invention have good paste stability with respect to both viscosity and syneresis, good body retention both during and after extrusion from the tube, and the paste breaks from the tube with very little stringiness.

The hydrophobically modified hydroxyethyl cellulose used in the compositions of this invention is a hydroxyethyl cellulose which is further substituted with a hydrocarbon radical having from 8 to 25 carbon atoms, preferably from 8 to 20 carbon atoms, in an amount, by weight of the hydrophobically modified hydroxyethyl cellulose, from about 0.1% to about 2.0%, preferably from about 0.4% to about 0.9%. Suitably the hydrophobically modified hydroxyethyl cellulose is employed in an amount, by weight of the composition, from about 0.1% to about 1.0%, preferably about 0.5% to about 1.0%.

The term "hydrocarbon radical" as used herein is meant to include the hydrocarbon portion as well as any other moiety present, such as an ester, ether, or urethane moiety, as a result of the particular compound used to further substitute the hydroxyethyl cellulose.

The hydroxyethyl cellulose to be modified can be low to high molecular weight, i.e., less than about 200,000 to about 400,000, preferably 280,000 to about 400,000, and has a hydroxyethyl M.S. of from about 2.5 to about 3.5, preferably about 2.9 to about 3.5. The designation M.S. refers to the average number of moles of hydroxyethyl substituent groups combined per cellulosic anhydroglucose unit of the cellulose molecule. The molecular weight is determined by extrapolation from the degree of polymerization. The molecular weight of the hydrophobically modified hydroxyethyl celluloses can be varied by degradation or depolymerization by any conventional means of degradation, such as treatment with peroxide, to obtain the desired molecular weight, either before or after substitutions with the hydroxyethyl and hydrophobic groups.

The hydrophobically modified hydroxyethyl cellulose can be prepared by the method set forth in U.S. Pat. No. 4,228,277.

The hydroxyethyl cellulose can be prepared by any known method, such as by treating a cellulose furnish with ethylene oxide in an alkaline medium. Any cellulose furnish can be used, such as wood pulp or chemical cotton. Typically the cellulosic furnish has a degree of polymerization (D.P.) from about 1300 to about 2300. D.P. is the number of anhydroglucose units in the cellulose backbone as determined by a five point intrinsic viscosity determination.

Gel toothpastes are partially broken down or deformed during the extrusion of the gel from the tube onto the toothbrush. As a result, the toothpaste does not break cleanly from the orifice or nozzle end of the tube upon extrusion and tends to flatten and sink into the bristles of the toothbrush. Polyethylene glycol has been added to overcome these deficiencies (see e.g., U.S. Pat. No. 3,934,000). Gel toothpastes containing polyethylene glycol generally have a yield value of about 3000 to 4000 dynes/cm$^2$ at a shear rate of about 1.8 to 2.1 sec$^{-1}$. Gel toothpastes are usually characterized by their yield value.

The hydrophobically modified hydroxyethyl cellulose can be combined with a polyethylene glycol having an average molecular weight from about 300 to about 20,000, preferably from about 300 to about 8000, in gel toothpastes. Typically the polyethylene glycol is present in gel toothpastes in an amount from about 1% to about 5%, preferably from about 1% to about 3%. Polyethylene glycols and the methods of preparing same are well known in the art.

Other conventional materials can be included in the compositions of this invention. For example, humectants, nonionic surfactants, coloring agents, whitening agents, flavoring agents, sweetening agents, preservatives, and chlorophyll-containing compounds. Humectants are generally included in toothpastes. Typical humectants include glycerin, sorbitol, propylene glycol or mixtures thereof which are admixed with a suitable humectant vehicle, such as water. The particular humectant will depend on whether the toothpaste is a cream or gel. The choice of the humectant is within the skill in the art. The humectant and vehicle mixture generally contains from about 50% to about 90% humectant and about 10% to about 50% vehicle. Humectants are used to retain moisture in the toothpaste, particularly at the nozzle end of the tube where the toothpaste can be in prolonged contact with the air. Typically the humectant is present in an amount from about 25% to about 60% and the vehicle for the humectant in an amount from about 15% to about 30%.

If a surfactant is used to impart detergency or foaming to the composition, only nonionic surfactants should be used to avoid compatability problems with the cationic bactericide. Typical nonionic surfactants include block copolymers of ethylene oxide and propylene oxide wherein the ratio of ethylene oxide units to propylene oxide units is 2:1.

Suitable flavoring agents include oils of peppermint, spearmint, and cinnamon. Sweetening agents, such as sodium saccharin; and preservatives, such as sodium benzoate, can be included in the toothpaste this invention. Any of these additives can be present in the toothpaste of this invention in an amount up to about 5%.

In addition, the compositions of this invention can contain a fluorine-containing compound in an amount sufficient to provide up to 1000 ppm fluoride ion content. Typical fluorine-containing compounds include sodium fluoride or sodium monofluorophosphate.

To further illustrate this invention, various illustrative examples are set forth below. All parts and percentages used in this specification are by weight, unless otherwise specified. All viscosity measurements are taken with a concentric cylinder viscometer at 25° C. and at 2.1 sec$^{-1}$.

It is not essential that the water used in the toothpaste compositions of this invention be distilled. However, it is industry practice to do so to insure that the hard tap water does not in any way interfere with the functioning of any of the ingredients in the toothpaste. Hence, distilled water is used in the illustrative examples.

EXAMPLE 1

This example illustrates an embodiment of the dentifrice composition of this invention and how to prepare it.

A mixing vessel equipped with a stirrer is charged with, by weight of the composition, 12.8% glycerin, 11.8% sorbitol solution (70% sorbitol in 30% water), and 1.0% hydrophobically modified hydroxyethyl cellulose having a hydroxyethyl M.S. of 3.3 and 0.4% of a $C_{16}$ hydrophobe substitution. The contents of the vessel are stirred for 10 minutes at 25° C. until a homogeneous blend is obtained. The vessel is then charged with 23.47% distilled water and stirred for 30 minutes at 25° C. Dicalcium phosphate, dihydrate (45.0%) is added and stirring continued for 5 minutes at 23° C. The vessel is then charged with 0.42% tetrasodium pyrophosphate, 0.20% sodium saccharin, 0.50% sodium benzoate and 0.76% sodium monofluorophosphate. The contents are mixed until a homogeneous blend is obtained (about 5 minutes). A peppermint flavoring agent (0.55%), a block copolymer of ethylene oxide and propylene oxide where the ratio of ethylene oxide units and propylene oxide units is 2:1 (3.0%) and benzethonium chloride (0.5%) are added to the vessel, and the contents are stirred under 26 inches of vacuum for about 30 minutes at 25° C. to deaerate the toothpaste and until a homogeneous blend is obtained. The resulting toothpaste has an initial viscosity of 45,900 centipoise (cps) at 2.1 sec$^{-1}$, a four-week viscosity of 126,300 cps at 2.1 sec$^{-1}$, and a thickener week viscosity of 200,300 cps. at 2.1 sec$^{-1}$. The texture is very short and smooth, i.e. little stringiness upon breaking from the tube after extrusion. There is no phase separation or syneresis after six months.

EXAMPLE 2

This example illustrates another embodiment of the composition of this invention.

The formulation and procedure of Example 1 are used except that the hydrophobically modified hydroxyethyl cellulose has a hydroxyethyl M.S of 3.5 and 0.64% of a $C_{16}$ hydrophobe substitution. The resulting toothpaste has an initial viscosity of 244,000 cps at 2.1 sec$^{-1}$ and a four-week viscosity of 172,300 cps at 2.1 sec$^{-1}$, and a somewhat elastic texture.

EXAMPLE 3

This example illustrates another embodiment of the composition of this invention.

The formulation and procedure of Example 1 are used except that the hydrophobically modified hydroxyethyl cellulose has 1.9% of a $C_8$ hydrophobe substitution. The resulting toothpaste has an initial viscosity of 479,100 at 2.1 sec$^{-1}$ and a four week viscosity of 548,800 at 2.1 sec$^{-1}$.

EXAMPLE 4

This example illustrates another embodiment of the composition of this invention.

The procedure and the formulation of Example 1 are used except that 0.6% of the hydrophobically modified hydroxyethyl cellulose is used instead of 1.0%, except that the hydrophobically modified hydroxyethyl cellulose has 1.9% of a $C_8$ hydrophobe substitution, and except that 23.87% distilled water is used instead of 23.47%. The resulting toothpaste has an initial viscosity of 120,600 cps at 2.1 sec$^{-1}$ and a four-month viscosity of 130,340 cps at 2.1 sec$^{-1}$. The texture is very short and there is no phase separation after four months.

EXAMPLE 5

This example illustrates another embodiment of the composition of this invention.

The formulation and procedure of Example 1 are used except that the hydrophobically modified hydroxyethyl cellulose used has 0.9% of a $C_{12}$ hydrocarbon radical substitution. The resulting toothpaste has an initial viscosity of 479,100 cps at 2.1 sec$^{-1}$ and a four-week viscosity of 522,600 cps at 2.1 sec$^{-1}$.

EXAMPLE 6

This example illustrates another embodiment of the composition of this invention.

The procedure and the formulation of Example 1 are used except that 0.6% of the hydrophobically modified hydroxyethyl cellulose is used instead of 1%, except that the hydrophobically modified hydroxyethyl cellulose used has 0.9% of a $C_{12}$ hydrocarbon radical substitution, and except that 23.87% distilled water is used instead of 23.47%. The resulting toothpaste has an initial viscosity of 143,500 cps at 2.1 sec$^{-1}$ and a four-month viscosity of 121,030 cps at 2.1 sec$^{-1}$. There is no phase separation or syneresis after one month.

EXAMPLE 7

This example illustrates another embodiment of the composition of this invention.

A mixing vessel equipped with a stirrer is charged with, by weight of composition, 2.9% distilled water, 25.0% glycerine, 42.2% sorbitol solution (70% sorbitol in 30% water), 3.0% of polyethylene glycol having a molecular weight of about 600, and 0.3% of a hydrophobically modified hydroxyethyl cellulose having a hydroxyethyl M.S. of 3.5 and 0.64% of a $C_{16}$ hydrocarbon substitution. The contents of the vessel are mixed at 20 inches of vacuum at 25° C. until a homogeneous blend is obtained (about 30 minutes). The vessel is then charged with 0.19% sodium saccharin, 0.50% sodium benzoate, 0.77% sodium monofluorophosphate. The contents of the vessel are mixed until a homogeneous blend is obtained (about 2 minutes). A silica xerogel (16.0%) having an average particle size of 8 microns, a surface area of about 320 m$^2$/g and a bulk density of about 0.26 g/cm$^3$ is added, and the contents of the vessel are mixed at 12 to 14 inches of vacuum for about 5 minutes until a homogeneous blend is obtained. The vessel is then charged with a silica aerogel (5.0%) having an average particle size of approximately 4 microns and a bulk density of about 0.11 g/cm$^3$. The contents of the vessel are mixed at 12 to 14 inches of vacuum for about 5 minutes until a homogeneous blend is obtained. A peppermint flavoring agent (0.55%), a block copolymer of ethylene oxide and propylene oxide where the ratio of ethylene oxide units to propylene oxide units is 2:1 (3.0%), and benzethonium chloride (0.5%) are added to the vessel, and the contents are stirred slowly at 26 inches of vacuum for about 30 minutes until a homogeneous blend is obtained. The resulting toothpaste has an initial yield value of 6700 dynes/cm$^2$ at a shear rate of 5 sec$^{-1}$ and a yield value of 5700 dynes/cm$^2$ at 5 sec$^{-1}$ after one month. In addition, the toothpaste has excellent body characteristics, i.e. stand up was excellent, very short texture, i.e. little stringiness upon breaking from the tube after extrusion, and no phase separation after one month.

The D.P. of the cellulose furnish used to prepare the hydrophobically modified hydroxyethyl cellulose of the examples is shown in the Table I below.

TABLE 1

| Example | 1 | 2 | 3 | 4 | 5 | 6 | 7 |
|---|---|---|---|---|---|---|---|
| Cellulose furnish D.P. | 1650 | 1330 | 1330 | 1330 | 2300 | 2300 | 1330 |

Thus, this invention provides a novel dentifrice composition or toothpaste having excellent viscosity stability and body characteristics upon storage and upon extrusion from the tube, as well as a lack of stringiness upon breaking from the tube.

Features, advantages and other specific embodiments of this invention will become readily apparent to those exercising ordinary skill in the art after reading the foregoing disclosures. In this regard, while specific embodiments of this invention have been described in considerable detail, variations and modifications of these embodiments can be effected without departing from the spirit and scope of the invention as disclosed and claimed.

What is claimed is:

1. In a dentifrice composition having water, a cationic bactericidal agent, a finely divided dental abrasive, and a thickener, the improvement which comprises as the thickener at least about 0.1% by weight of a hydrophobically modified hydroxyethyl cellulose which is hydrophobically modified with a hydrocarbon radical having 8 to 25 carbon atoms in an amount from about 0.1 to about 2.0% and has a hydroxyethyl M.S. of from about 2.5 to about 3.5.

2. The composition of claim 1 wherein the hydrophobically modified hydroxyethyl cellulose is present in an amount from about 0.1% to about 1.0% by weight of the composition.

3. The composition of claim 1 which further comprises a nonionic surfactant.

4. The composition of claim 1 whereas the hydrophobically modified hydroxyethyl cellulose is hydrophobically modified with a hydrocarbon radical having 8 to 20 carbon atoms.

5. In a dentifrice composition having water, a cationic bactericidal agent, a finely divided dental abrasive, a humectant, a vehicle for the humectant and a thickener, the improvement which comprises as the thickener at least about 0.1% by weight of a hydrophobically modified hydroxyethyl cellulose which is hydrophobically modified with a hydrocarbon radical having 8 to 25 carbon atoms in an amount from about 0.1 to about 2.0% and has a hydroxyethyl M.S. of from about 2.5 to about 3.5.

6. The composition of claim 5 wherein the hydrophobically modified hydroxyethyl cellulose is present in an amount from about 0.1% to about 1.0% by weight of the composition.

7. The composition of claim 5 which further comprises a silica thickening agent.

8. The composition of claim 5 which further comprises a polyethylene glycol having a molecular weight of from about 300 to about 20,000.

9. The composition of claim 8 wherein the polyethylene glycol is present in an amount of 1% to about 5% by weight of the composition.

* * * * *